(12) United States Patent
Weyl et al.

(10) Patent No.: US 7,434,448 B2
(45) Date of Patent: Oct. 14, 2008

(54) SENSOR

(75) Inventors: Helmut Weyl, Wiesbaden (DE); Juergen Wilde, Fellbach (DE); Andreas Pesch, Krefeld (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/557,406

(22) PCT Filed: Apr. 16, 2004

(86) PCT No.: PCT/DE2004/000798

§ 371 (c)(1), (2), (4) Date: Aug. 21, 2006

(87) PCT Pub. No.: WO2004/109270

PCT Pub. Date: Dec. 16, 2004

(65) Prior Publication Data

US 2007/0056353 A1 Mar. 15, 2007

(30) Foreign Application Priority Data

Jun. 3, 2003 (DE) ................................ 103 24 956

(51) Int. Cl.
*G01N 27/26* (2006.01)
*G01M 15/10* (2006.01)
(52) U.S. Cl. ...................... 73/23.31; 73/31.05; 204/424; 204/426; 204/428
(58) Field of Classification Search ................ 73/23.31, 73/31.05; 204/424, 426, 428, 431
See application file for complete search history.

(56) References Cited

U.S. PATENT DOCUMENTS

| 3,616,416 | A | * | 10/1971 | Linenberg et al. | ............ 204/409 |
| 4,187,163 | A | * | 2/1980 | Steinke et al. | ................ 204/428 |
| 4,507,192 | A | * | 3/1985 | Ebizawa et al. | ............. 204/428 |
| 5,739,414 | A | | 4/1998 | Paulus et al. | ................ 73/23.31 |
| 5,955,656 | A | | 9/1999 | Graser et al. | ................ 73/23.31 |
| 6,319,376 | B1 | * | 11/2001 | Graser et al. | ................ 204/424 |
| 6,672,132 | B1 | * | 1/2004 | Weyl et al. | ................. 73/23.31 |

FOREIGN PATENT DOCUMENTS

| CH | 689741 | * | 9/1999 |
| DE | 25 04 207 | | 8/1976 |
| DE | 43 18 107 | | 12/1994 |
| DE | 197 05 402 | | 1/1998 |
| DE | 197 39 435 | | 3/1999 |
| DE | 102 10 313 | | 10/2003 |
| EP | 0 458 368 | | 11/1991 |
| EP | 1 215 385 | | 6/2002 |
| JP | 2002-350238 | * | 12/2002 |

\* cited by examiner

*Primary Examiner*—Daniel S Larkin
(74) *Attorney, Agent, or Firm*—Kenyon & Kenyon LLP (57) ABSTRACT

A sensor for determining a physical property such as the concentration of a gas component or the temperature of a measuring gas, e.g., the exhaust gas of internal combustion engines, has a sensor element which is secured in a housing and is surrounded at an end section on the measuring gas side by a protective tube and surrounded at an end section on the connection side by a protective sleeve, and also has a radially projecting flange for securing the sensor on a sealing seat formed on a measuring gas duct. To reduce manufacturing costs, the flange is molded onto the protective tube as one piece. The protective tube is manufactured as a deep-drawn part, and a trimming edge remaining after deep drawing on the end side is used as a securing flange.

11 Claims, 6 Drawing Sheets

SENSOR

FIELD OF THE INVENTION

The present invention relates to a sensor for determining a physical property such as the concentration of a gas component or the temperature of a measuring gas, e.g., the exhaust gas of internal combustion engines.

BACKGROUND INFORMATION

Published German patent document DE 43 18 107 describes a sensor for detecting gases flowing in a gas duct, in which the housing that accommodates the sensor element is designed as a tubular metal housing having a longitudinal bore. The outer periphery of the metal housing has a single-piece peripheral flange, which is used for securing the metal housing on a sealing seat formed on the gas duct. A central section of the sensor element is inserted centrally into the metal housing and is secured via a sealing system which presses against both the sensor element and the bore wall of the longitudinal bore, an end section on the measuring gas side and an end section on the connection side of the sensor element projecting from the housing on both sides of the housing. A connecting plug which connects the sensor element to connecting cables is mounted on the connection side end section. The end section on the connection side having connecting plugs is covered by a protective sleeve which is pushed over the metal housing and welded thereto. The end section of the sensor element on the measuring gas side is surrounded by a protective tube having gas passage openings, the housing side end of the protective tube carrying an annular flange pointing outward which is fastened inside the metal housing.

In another sensor for determining the oxygen level in exhaust gases of internal combustion engines, which sensor is described in published German patent document DE 197 39 435, the sensor element is installed in a tubular metal housing on which a sealing flange is formed by first upsetting the tubular element, forming a rounded bulge, and subsequently machining the bulge by swaging in such a way that two sealing surfaces, inclined with respect to one another and axially surrounding the housing, are formed. The sensor element is secured in the housing via a sealing system having a ceramic molded part on the measuring gas side, a ceramic molded part on the connection side, and a sealing element therebetween, and gas-tightly sealed in such a way that the end section of the sensor element on the measuring gas side projects out from the housing. The ceramic molded parts are made of aluminum oxide ($Al_2O_3$) and have central bushings for the sensor element. The sealing element made of steatite, which also has a bushing for the sensor element, is inserted, in a pre-pressed state, between the ceramic molded parts. Subsequently, pressure is applied on the ceramic molded part on the measuring gas side using a punch to crush the pre-pressed sealing element and press it onto the housing wall and the sensor element. Subsequently the inside of the housing is shaped to hold the pressure position with respect to the sealing element. The ceramic molded part on the connection side is supported by a radial shoulder inside the housing. A double protective tube having gas passage openings is reverse drawn over the end section on the measuring gas side, its end being pushed into the housing and welded thereto. In the installed position, the sealing flange of the housing rests on a sealing seat formed in a connecting piece of the exhaust pipe and is secured using a cap screw whose annular surface rests on the sealing flange and which is screwed onto an external thread of the connecting piece. The connecting piece gas-tightly surrounds an insertion hole, situated in the measuring gas duct, i.e., the exhaust pipe, for the double protective tube.

SUMMARY

The sensor according to the present invention has the advantage that the enclosure of the sensor element, which is also used for mounting the sensor on the measuring gas duct, is made up of components which may be manufactured using very simple and cost-effective manufacturing methods and joined in a few assembly steps.

According to an example embodiment of the present invention, the protective sleeve and/or the protective tube are manufactured as deep-drawn parts, the deep draw or trimming edge which is usually removed after deep drawing being used as a securing flange for securing the sensor in the sealing seat of the measuring gas duct. Stainless refractory steels or nickel alloys are used as materials for the deep-drawn parts. After deep drawing, part of the trimming edge situated in the held-down area outside the deep-drawing mold is punched out or cut off, so that the flange has a defined radial dimension. The two deep-drawn parts are assembled with, and welded to, the housing manufactured as a simple tube.

Alternatively, it is possible to provide only the protective sleeve or only the protective tube with a flange. Providing only one sealing flange on one of the two components makes it possible to use a manufacturing method other than deep-drawing for the other component.

If both trimming edges on the deep-drawn parts are used as flanges, the flange on the protective tube forms the securing flange for the sealing seat of the measuring gas duct, while the flange on the protective sleeve assumes the function of an anti-loss device for a hollow screw pushed onto the housing. The hollow screw is pushed onto the housing prior to joining the protective sleeve and the housing. One end face of the hollow screw has an annular stop surface, which may rest on the protective sleeve on the bottom of the flange facing the housing, and on the other end face has an annular securing surface, which may rest on the flange on the protective tube.

According to an advantageous embodiment of the present invention, the housing is formed by an internal protective tube surrounding the end of the sensor element on the measuring gas side, the internal protective tube being in turn concentrically surrounded by the protective tube. One end of the internal protective tube facing the protective sleeve carries a single-piece flange, which is joined to the two flanges on the protective tube and on the protective sleeve and is secured on the sealing seat. This arrangement replaces the double protective tube for the end section of the sensor element on the measuring gas side, which is often used in exhaust gas sensors, and the function of the housing, a component being made superfluous by the non-existence of the housing. The total of three components, i.e., internal protective tube, protective tube, and protective sleeve, are joined to form the enclosure of the sensor element and held joined in the flange area by securing them on the sealing seat. Additional welds for producing a laser welded overlap weld or an axial I weld, or a fillet weld, for example, between protective sleeve and protective tube are not needed. This reduces both the investment outlay and the manufacturing time for the manufacture of the sensor. At the same time, greater flexibility in the dimension of the sensor element projecting into the measuring gas and a cost-effective shortening of the sensor element are achieved.

DETAILED DESCRIPTION

Figure 1:
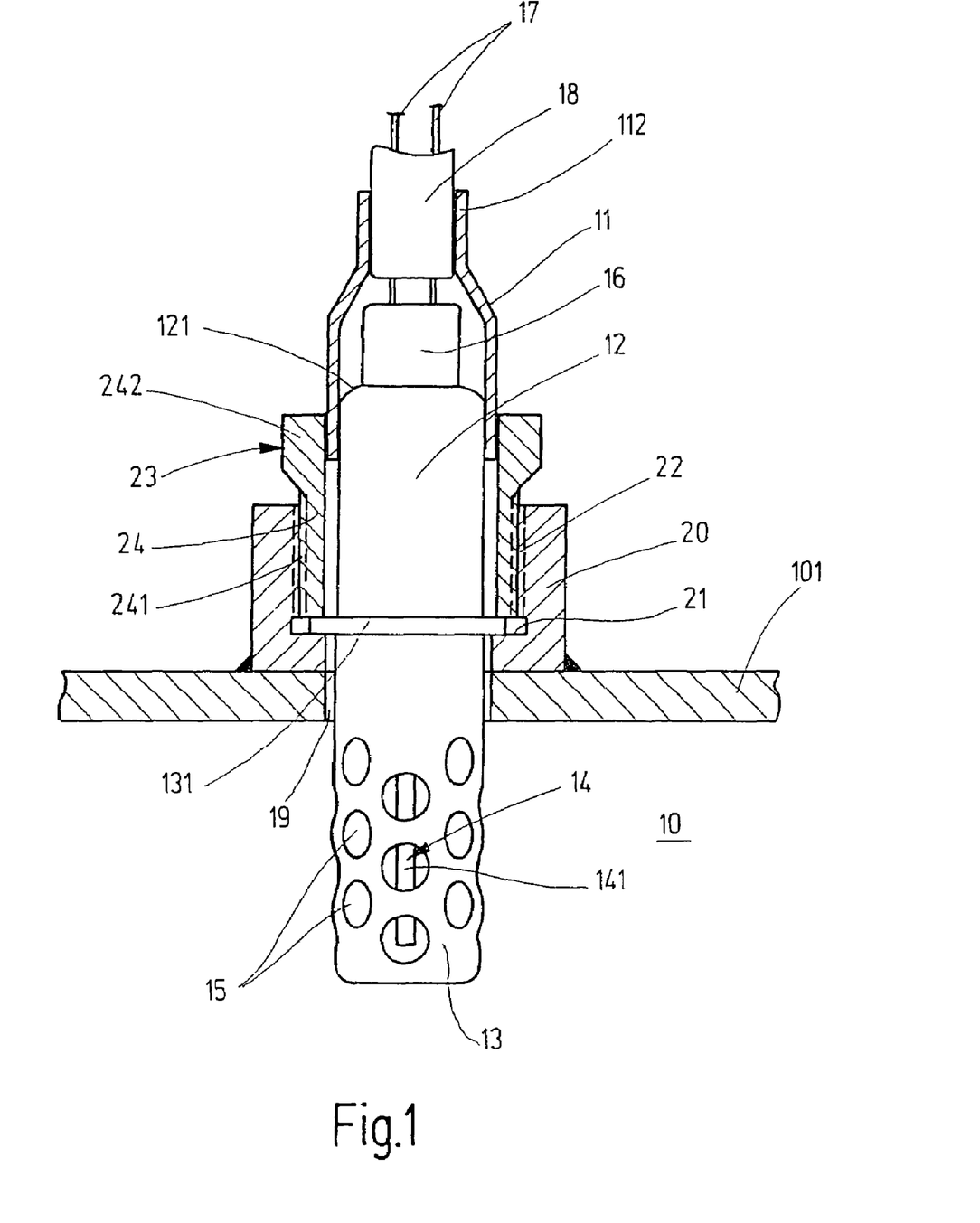
FIGS. 1 through 5 show partial cross-sectional views of five different exemplary embodiments of an exhaust gas sensor inserted into an exhaust pipe.
Figure 6:
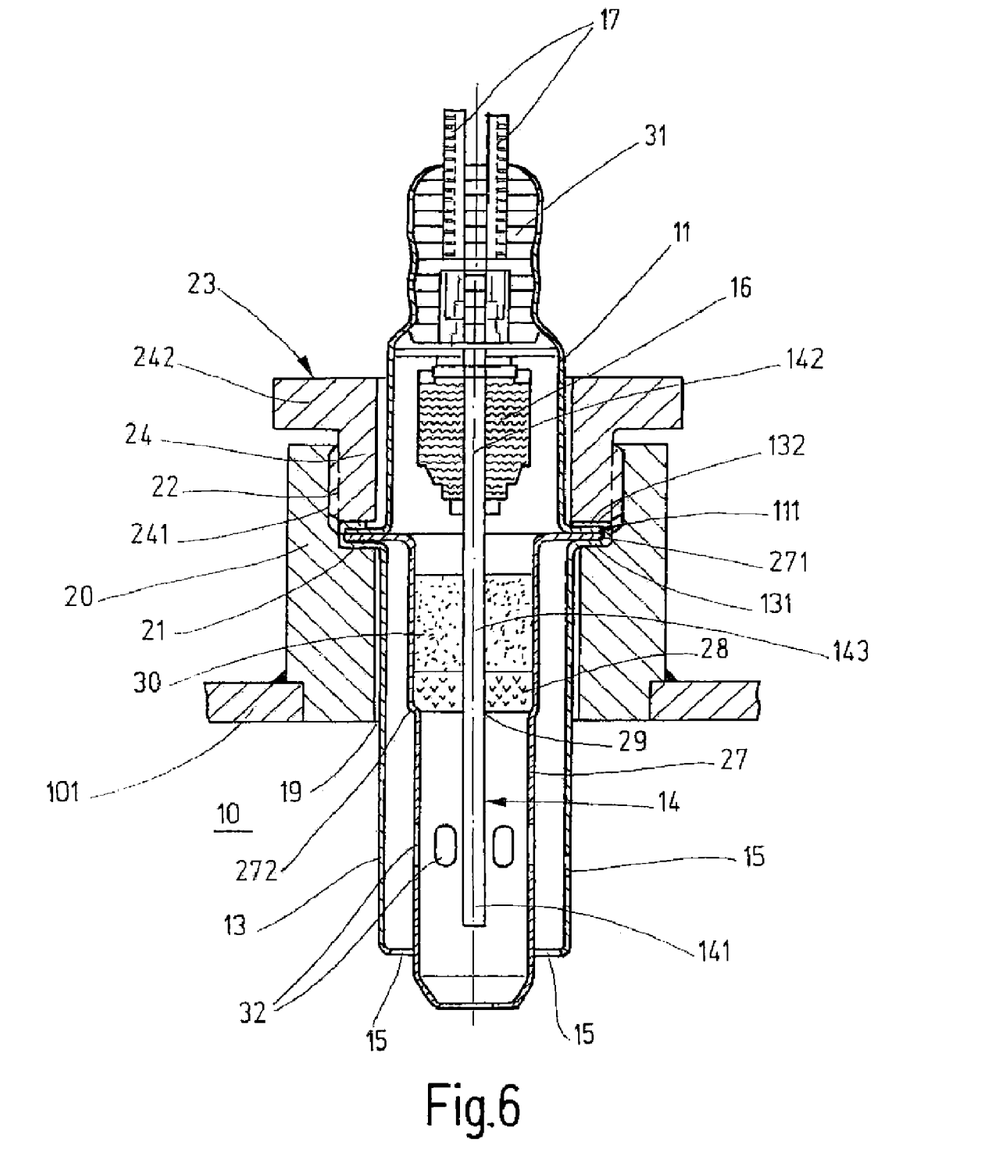
FIG. 6 shows a longitudinal cross-sectional view of an exhaust gas sensor inserted into an exhaust pipe according to an exemplary embodiment.

The exhaust gas sensor shown in FIG. 1 is depicted in its installed position in an exhaust pipe 10 of a motor vehicle as an exemplary embodiment of a generic sensor for determining a physical property of a measuring gas, which sensor is used as a lambda sensor for determining the oxygen concentration in the exhaust gas of internal combustion engines. The exhaust gas sensor has a sensor element 14, which is surrounded by an enclosure composed of a protective sleeve 11, a tubular housing 12, and a protective tube 13. Sensor element 14, only an end section 141 of which is visible in FIG. 1 on the measuring gas side through gas passage holes 15 in protective tube 13, is depicted in its entirety in FIG. 6. As FIG. 6 shows, the other, connection side, end section 142 of sensor element 14 is electrically connected to connecting cables 17 via a connecting plug 16. In the exemplary embodiments of FIGS. 1 through 5, connecting cables 17 are surrounded by a sheathing tube 18. Protective sleeve 11 is manufactured as an extruded or deep-drawn part and has a tapering section 112, into whose opening sheathing tube 18 is introduced and fastened by welding, for example. Housing 12 is manufactured from a tube and is crimped at its upper end inserted into protective sleeve 11. Crimping edge 121 supports a gasket not shown in FIG. 1, which gas-tightly surrounds sensor element 14 and presses against the internal wall of housing 12. Protective tube 13 is manufactured as a deep-drawn part which carries annular flange 131 on its end pushed onto the lower end of housing 12 and forms a single piece with this flange. This flange 131 is formed by the trimming edge present after deep-drawing, which is usually cut off from deep-drawn components. However, in the present case of protective tube 13, the trimming edge remains on protective tube 13. The starting material for manufacturing protective tube 13 is a 0.3 mm to 0.6 mm thick sheet of stainless, refractory steel or a nickel alloy, for example, the area of the trimming edge held down outside the mold being punched out or cut after deep drawing, the cut running at a distance of approximately 1.5 mm from the outer contour of protective tube 13, for example. Protective tube 13 and protective sleeve 11 are pushed onto opposite end areas of housing 12 and fixedly attached thereto by laser beam welding, for example.

To receive the exhaust gas sensor, tube wall 101 of exhaust pipe 10 has an insertion opening 19, which is concentrically surrounded by a connecting piece 20. Hollow cylindrical connecting piece 20 is welded to tube wall 101 and is provided with a sealing seat 21 for placing flange 131 on protective tube 13 and with an internal thread 22 for screwing in a bracing element 23 designed as a hollow screw 24. Hollow screw 24 is used for securing the exhaust gas sensor in connecting piece 20.

To install the exhaust gas sensor into exhaust pipe 10, the exhaust gas sensor, together with protective tube 13, is inserted through connecting piece 20 and insertion opening 19 in tube wall 101 until flange 131 on protective tube 13 comes to rest on sealing seat 21. Hollow screw 24, pushed over protective sleeve 11 and housing 12, is now screwed into internal thread 22 by the hollow screw's external thread 241, its front annular face coming to rest on flange 131 on protective tube 13 and securing it against sealing seat 21. Hollow screw 24 has a hex surface 242 for receiving a wrench for screwing the screw 24 into connecting piece 20.

Figure 2:
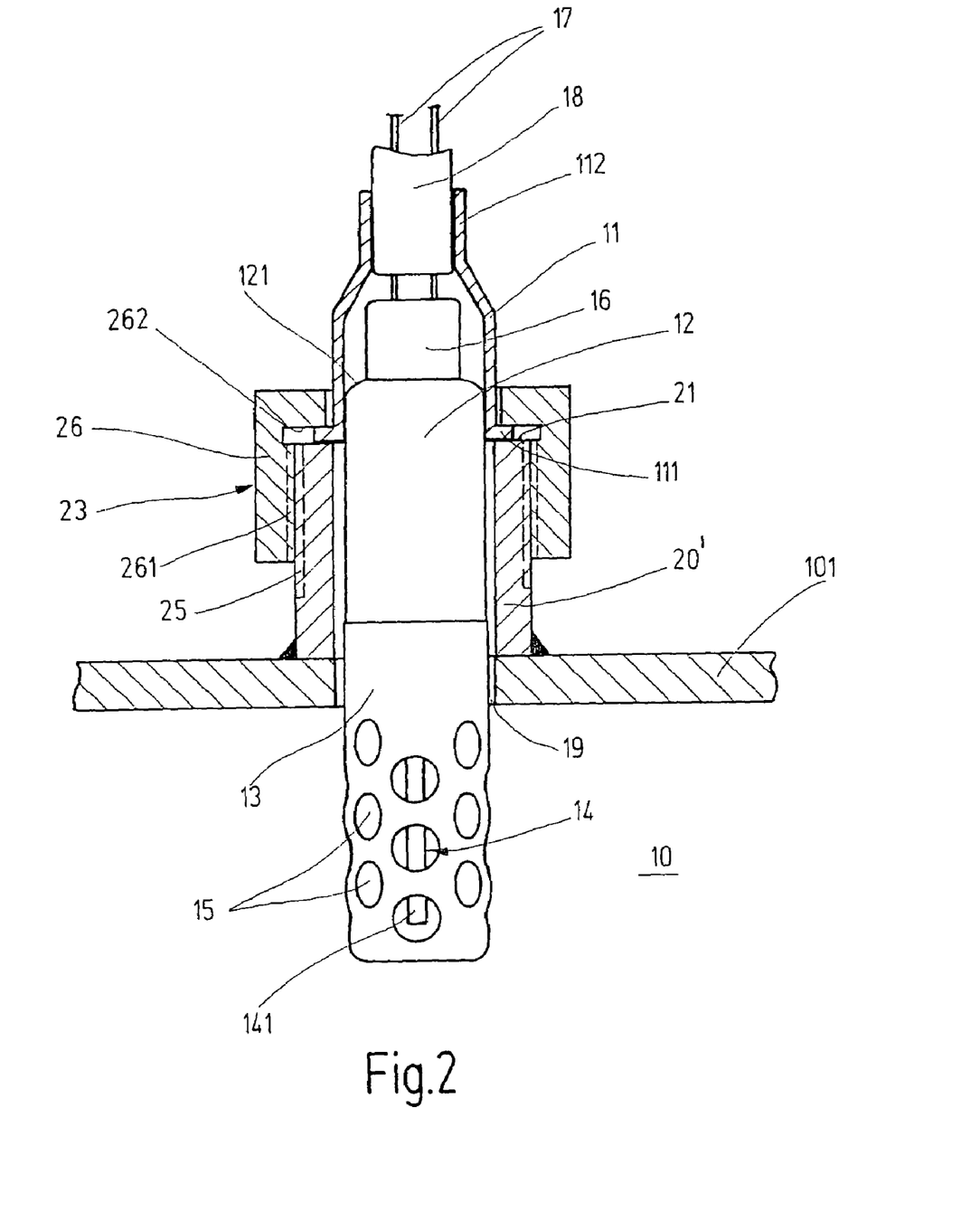

The exhaust gas sensor depicted in FIG. 2 has the same design as described above, however, with the difference that instead of protective tube 13, protective sleeve 11, also manufactured as a deep-drawn part, carries an annular flange 111, forming with it a single piece. In this case, as described for the protective tube of FIG. 1, flange 111 is formed from the trimming edge remaining after deep-drawing. However, the trimming edge is removed from protective tube 13 as usual after deep drawing. Protective sleeve 11, housing 12, and protective tube 13 are in turn permanently bonded, e.g., welded together, and enclose sensor element 14. When the exhaust gas sensor is installed into exhaust pipe 10, the exhaust gas sensor, together with protective tube 13, is inserted through insertion opening 19 until flange 111 on protective sleeve 11 comes to rest on sealing seat 21 formed on connecting piece 20'. Connecting piece 20' carries an external thread 25, and bracing element 23 is designed as a cap screw 26 having an internal thread 261, using which cap screw 26 is threadable on connecting piece 20'. Cap screw 26 has, near to its front face, a radial shoulder 262, which, after cap screw 26 is mounted on protective sleeve 11 and threaded onto connecting piece 20', rests on flange 111 of protective sleeve 11.

To install the exhaust gas sensor into exhaust pipe 10, the exhaust gas sensor, together with protective tube 13, is in turn inserted through insertion opening 19 in tube wall 101 until flange 111 on protective sleeve 11 comes to rest on sealing seat 21. Cap screw 26 surrounding protective sleeve 11 is then threaded onto connecting piece 20' until its radial shoulder 262 secures flange 111 of protective sleeve 11 on sealing seat 21. Otherwise the design of the exhaust gas sensor according to FIG. 2 is substantially identical to that of FIG. 1, so that the same components are provided with the same reference symbols.

Figure 3:
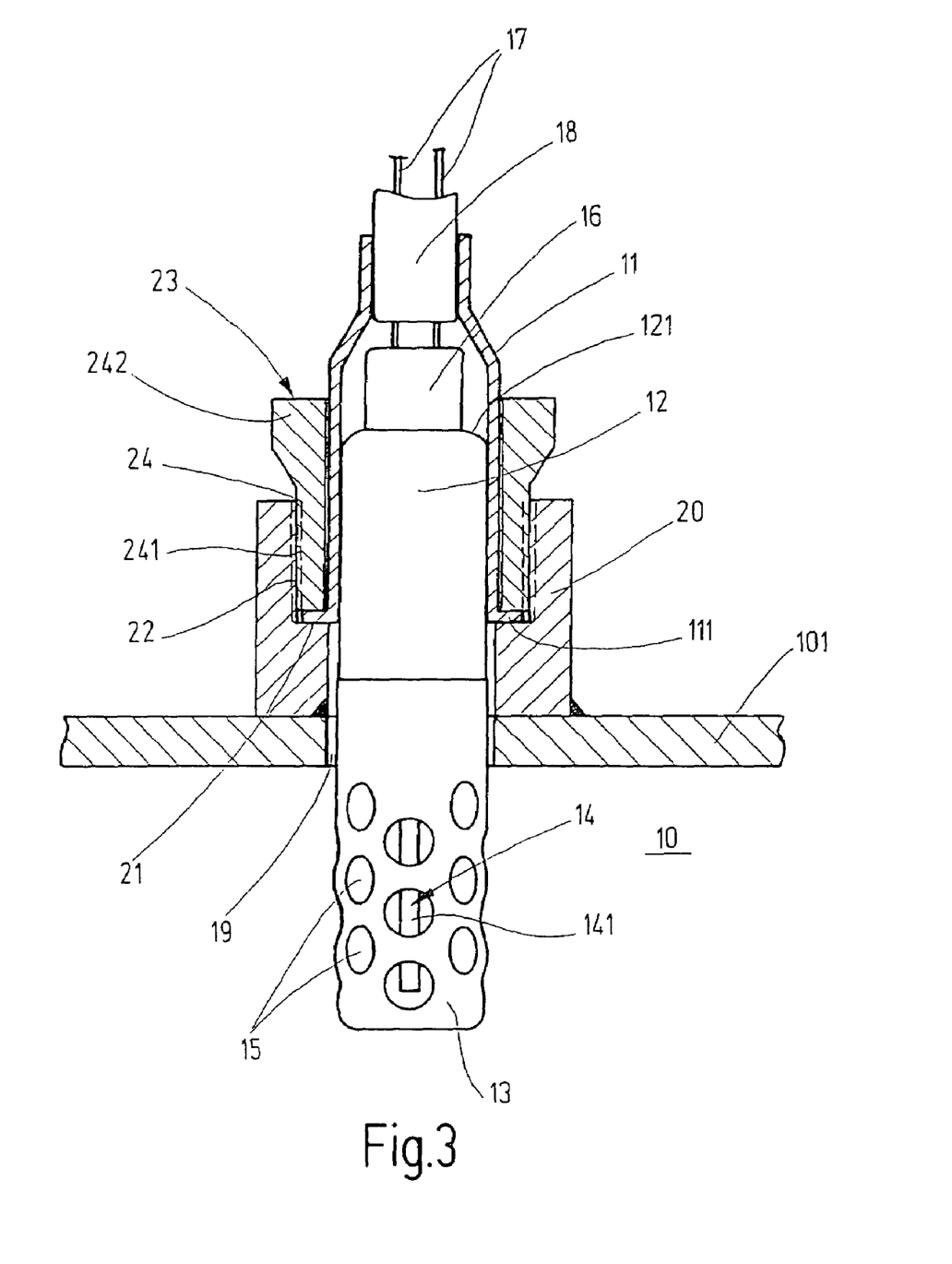

In the exemplary embodiment of the exhaust gas sensor depicted in FIG. 3, in contrast with the exemplary embodiment of FIG. 2, the bracing element designed in the latter as a cap screw is designed here as a hollow screw 24 which, as in FIG. 1, is threadable in connecting piece 20. Flange 111 on protective sleeve 11 of the exhaust gas sensor rests on gasket 21 formed in connecting piece 20 and is secured with respect to connecting piece 20 when hollow screw 24 is threaded over the front annular surface of hollow screw 24. Using flange 111 on protective sleeve 11 obtained by deep drawing as a securing flange, as is the case in FIGS. 2 and 3, results in advantages compared to the use of flange 131 on protective tube 13 as a securing flange according to FIG. 1, since protective sleeve 11 is usually manufactured with a thicker wall than protective tube 13.

Figure 4:
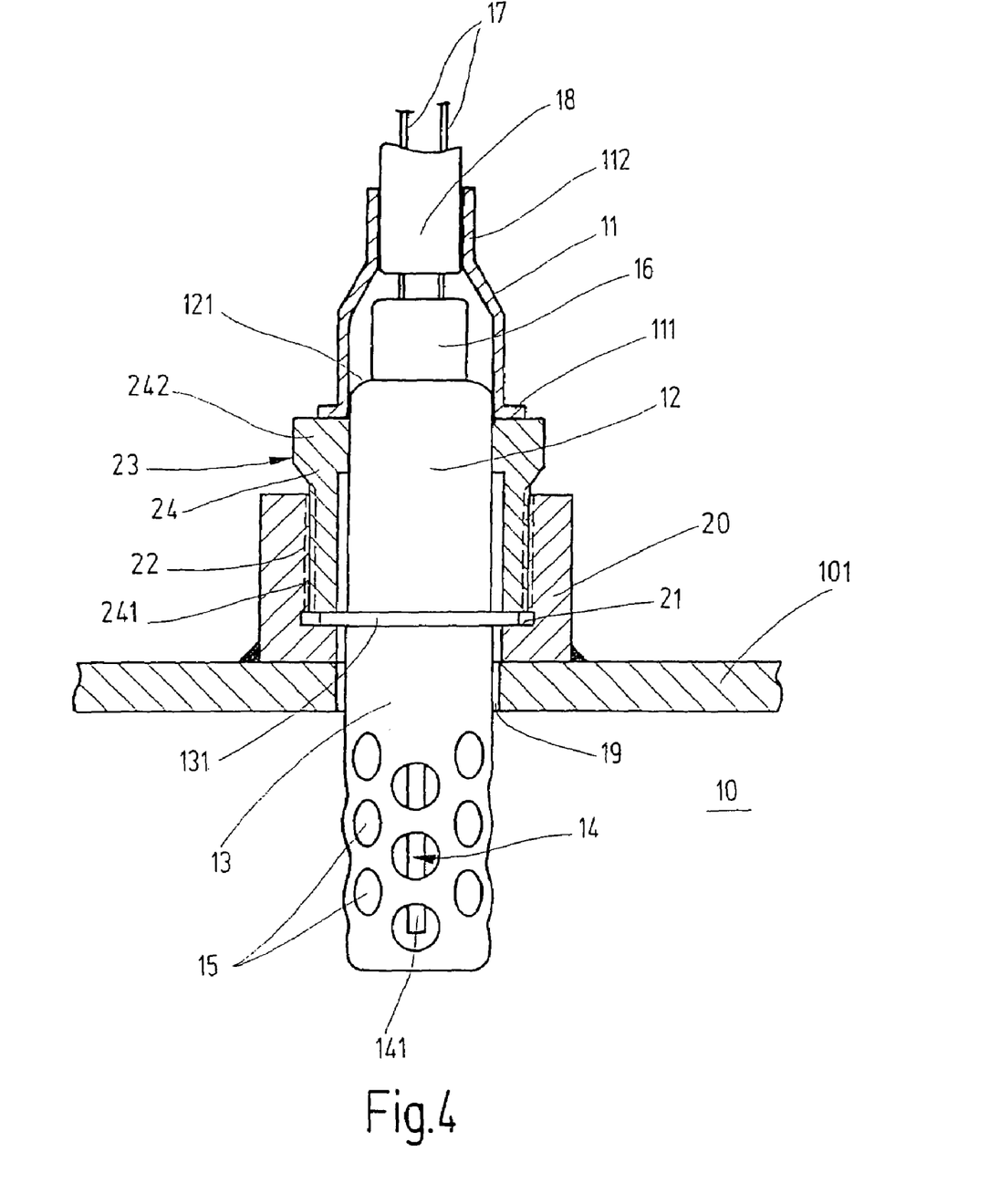
Figure 5:
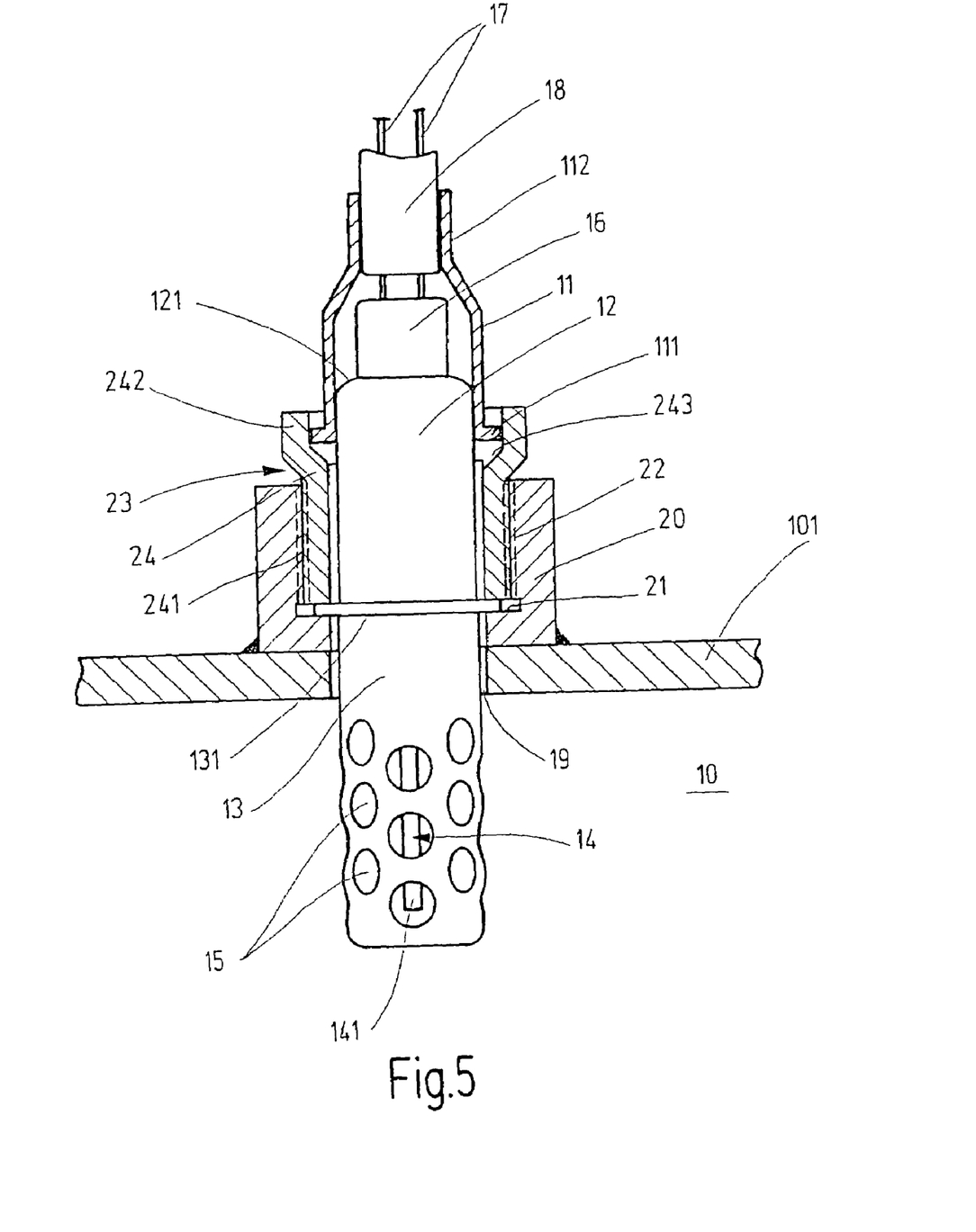

The exemplary embodiments of an exhaust gas sensor mounted on exhaust pipe 10 shown in FIGS. 4 and 5 are almost identical to the exemplary embodiment described in reference to FIG. 1, with the exception that the trimming edge present after deep drawing on protective sleeve 11, which is manufactured as the deep-drawn part, is left intact and is punched out or cut to approximately 1.5 mm, for example, from the outer contour of the sleeve. Flange 111 is used as a stop for hollow screw 24 and forms an anti-loss device for hollow screw 24. In both cases, according to FIGS. 4 and 5, hollow screw 24 is pushed onto housing 12 permanently bonded to protective tube 13 prior to joining protective sleeve 11 and housing 12. Protective sleeve 11 is then pushed over the end of housing 12 and welded to housing 12. Hollow screw 24 is now captured between the two flanges 111 and 131 on protective sleeve 11 and protective tube 13, respectively, with an axial clearance. In the exemplary embodiment of FIG. 4, the free end face of hollow screw 24 facing away from protective tube 13 is supported by flange 111 of protective sleeve 11, while in the exemplary embodiment of FIG. 5, hollow screw 24 has an enlarged, internal diameter in the area of its hex surface 242 which is slightly larger than the external diameter of flange 111 on protective sleeve 11. In the transition area from hex surface 242 to the threaded area, a circumferential beveled shoulder 243 is formed, which comes into contact with flange 111 of protective sleeve 11 when hollow screw 24 moves axially on housing 12.

To install the exhaust gas sensor according to FIGS. 4 and 5, the exhaust gas sensor, together with protective tube 13, is again inserted through insertion opening 19 into tube wall 101 of exhaust pipe 10 until external thread 241 of hollow screw 24 engages with internal thread 22 of connecting piece 20. The exhaust gas sensor is then displaced axially downward by turning hollow screw 24 until flange 131 on protective tube 13 comes to rest on sealing seat 21 of connecting piece 20. Further turning of hollow screw 24 results in flange 131 being non-positively secured on sealing seat 21.

In the exhaust gas sensor depicted in FIG. 6 in its installed position in exhaust pipe 10, housing 12 in which sensor element 14 is installed is designed as an internal protective tube 27, which surrounds end section 141 of sensor element 14 on the measuring gas side and is in turn surrounded by protective tube 13. In the surrounded area, internal protective tube 27 is provided with gas passage holes 32. Internal protective tube 27, like protective tube 13 and protective sleeve 11, is manufactured as a deep-drawn part, the trimming edge being left intact in all three deep-drawn parts and trimmed to a certain distance from the sleeve wall or protective tube wall. The external area of flange 131 on protective tube 13 is used as a crimping edge 132.

Central section 143 of sensor element 14 is secured in the upper area of internal protective tube 27, which assumes the function of housing 10 and has a somewhat larger internal diameter than the lower area of internal protective tube 27, so that an annular shoulder 272 results at the transition between the two tube areas. A ceramic disk 28 having a central passage hole 29 for sensor element 14 is supported by this shoulder 272. A gasket 30, which sealingly surrounds sensor 14 and presses on the internal wall of internal protective tube 27, rests on ceramic disk 28. This gasket 30 is made of sealing glass or temperature resistant cement or a foamy ceramic compound. In the manufacture of gasket 30, ceramic disk 28, which is made of fosterite, for example, prevents the sealing glass or cement from running out. If a foamy ceramic compound is used, a second ceramic disk, which prevents the foam from escaping during the heating process, is mounted over gasket 30. The component made up of internal protective tube 27 and sensor element 14 secured therein is inserted into protective tube 13 in such a way that flange 271 of internal protective tube 27 comes to rest on flange 131 of protective tube 13. Protective sleeve 11 is then reverse drawn over end section 142 of sensor element 14 mounted in connecting plug 16 on the connection side, and its flange 111 is made to rest on flange 271 of internal protective tube 27. Crimping edge 132 on flange 131 of protective tube 13 is then crimped onto flange 111 of protective sleeve 11. The tapered end section of protective sleeve 11 is pressed onto an elastic plug-like molded part 31 surrounding connecting cable 17 to connecting plug 16.

The exhaust gas sensor assembled in this way is mounted on exhaust pipe 10 as described with reference to FIG. 1 by inserting protective tube 13 into exhaust pipe 10 again through insertion opening 19 in connecting piece 20 attached to the wall of exhaust pipe 10 until flange 131 on protective tube 13 comes to rest on sealing seat 21 formed on connecting piece 20. Hollow screw 24 is then threaded into connecting piece 20. The annular front surface of hollow screw 24 presses on crimping edge 132 of protective tube 13 in such a way that the exhaust gas sensor is non-positively secured in connecting piece 20.

Crimping edge 132 formed on flange 131 of protective tube 13 makes it possible to pre-manufacture the exhaust gas sensor as a component, which may then be inserted into exhaust pipe 10 of the engine on site. Of course, it is possible to omit crimping edge 132 and place flanges 131, 271, and 111 of the three deep-drawn parts enclosing sensor element 14 on one another, joining them using hollow screw 24. A welded joint between the deep-drawn parts may be omitted both in the case of peripheral crimping and simple joining, which reduces the investment costs in manufacturing and makes it possible to achieve shorter cycle times in manufacturing. By replacing the expensive housing, often manufactured as a turned part, by the internal protective tube manufactured as an extruded or deep-drawn part, fewer components and more cost-effective manufacture result, in particular in the case of exhaust gas sensors in which a double protective tube is required for the measuring gas side of end section 141 of sensor element 24.

The present invention is not restricted to the exemplary sensors described above, designed as exhaust gas sensors. It may be equally used, offering the same advantages, for the manufacture of the enclosures of sensor elements in temperature sensors, pressure sensors and similar sensors. A temperature sensor is described in published German patent document DE 37 33 192, for example.

Furthermore, instead of hollow screw 24 or cap screw 26, a bracing element 23 of some other design may also be used. In that case the flange on protective tube 14 or protective sleeve 11 itself does not need to rest on sealing seat 21 of connecting piece 20. For example, a beveled shoulder of housing 12 may also rest on sealing seat 21, forming a gas-tight seat, bracing element 23 engaging, as previously, the flange on protective sleeve 11 or protective tube 13, attaching it to connecting piece 20.

What is claimed is:

1. A sensor for determining a physical property of an exhaust gas of an internal combustion engine, comprising:
   a housing;
   a sensor element secured in the housing, wherein a first end section of the sensor element on a measuring gas side is enclosed by a protective tube, and wherein a second end section of the sensor element on a connection side is further enclosed by a protective sleeve; and
   at least one radially-projecting flange for securing the sensor on a sealing seat formed on a measuring gas duct, wherein the at least one radially-projecting flange is formed as one piece on at least one of the protective sleeve and the protective tube;
   wherein the protective sleeve and the protective tube are manufactured as deep-drawn parts, and a trimming edge remaining after deep drawing forms the at least one radially-projecting flange; and
   wherein at least one of:
   a) a first radially-projecting flange is attached to the protective tube using a hollow screw mounted radially surrounding the housing and the protective sleeve, and wherein an annular end face of the hollow screw rests on the first radially-projecting flange; and b) a second radially-projecting flange is integrally formed on the protective sleeve, wherein the second radially-projecting flange forms a stop that prevents the hollow screw from being removed from surrounding the housing.

2. The sensor as recited in claim 1, wherein a first area of the housing is permanently fixed to the protective sleeve and a second area of the housing is permanently fixed to the protective tube.

3. The sensor as recited in claim 2, further comprising:
a bracing element that engages the radially-projecting flange, wherein the bracing element is configured as one of a hollow screw and a cap screw.

4. A sensor for determining a physical property of an exhaust gas of an internal combustion engine, comprising:
a housing;
a sensor element secured in the housing, wherein a first end section of the sensor element on a measuring gas side is enclosed by a protective tube, and wherein a second end section of the sensor element on a connection side is further enclosed by a protective sleeve; and
at least one radially-projecting flange for securing the sensor on a sealing seat formed on a measuring gas duct, wherein the at least one radially-projecting flange is formed as one piece on at least one of the protective sleeve and the protective tube;
wherein the protective sleeve and the protective tube are manufactured as deep-drawn parts, and a trimming edge remaining after deep drawing forms the at least one radially-projecting flange; and
wherein the housing is formed by an additional internal protective tube enclosing the first end section of the sensor element on the measuring gas side, the additional internal protective tube being in turn enclosed by the protective tube and including a single-piece flange at an end facing the protective sleeve, and wherein a first radially-projecting flange on the protective tube, a second radially-projecting flange on the protective sleeve, and the single-piece flange on the additional internal protective tube are engaged to one another and secured on the sealing seat.

5. The sensor as recited in claim 4, wherein the first radially-projecting flange on the protective tube has a single-piece crimping edge that is crimped onto the second radially-projecting flange on the protective sleeve, and the single-piece flange on the additional internal protective tube is secured between the first and second radially-projecting flanges.

6. The sensor as recited in claim 5, wherein the first radially-projecting flange on the protective tube is secured onto the sealing seat by a bracing element resting on the single-piece crimping edge and concentrically surrounding the protective sleeve.

7. The sensor as recited in claim 4, wherein the sensor element is hermetically sealed against an internal wall of the additional internal protective tube by one of a sealing glass, a temperature-resistant cement, and a foamy ceramic compound.

8. The sensor as recited in claim 7, wherein the additional internal protective tube has a first tube section and a second tube section, the diameter of the first tube section being smaller than the diameter of the second tube section, and wherein a first ceramic disk having a central passage hole for the sensor element is placed in the second tube section having the larger diameter, and wherein the first ceramic disk is supported by a shoulder section of the additional internal protective tube formed between the first and second tube sections.

9. The sensor as recited in claim 8, wherein an opening of the additional internal protective tube on the side of the single-piece flange is covered by a second ceramic disk having a central passage hole for the sensor element, and wherein a gap between the first and second ceramic disks is filled with foamed ceramic compound.

10. A sensor for determining a physical property of an exhaust gas of an internal combustion engine, comprising:
a housing;
a sensor element secured in the housing, wherein a first end section of the sensor element on a measuring gas side is enclosed by a protective tube, and wherein a second end section of the sensor element on a connection side is further enclosed by a protective sleeve; and
at least one radially-projecting flange for securing the sensor on a sealing seat formed on a measuring gas duct, wherein the at least one radially-projecting flange is formed as one piece on at least one of the protective sleeve and the protective tube;
wherein the protective sleeve and the protective tube are manufactured as deep-drawn parts, and a trimming edge remaining after deep drawing forms the at least one radially-projecting flange;
wherein the housing is formed by an additional internal protective tube enclosing the first end section of the sensor element on the measuring gas side, the additional internal protective tube being in turn enclosed by the protective tube and including a single-piece flange at an end facing the protective sleeve, and wherein a first radially-projecting flange on the protective tube, a second radially-projecting flange on the protective sleeve, and the single-piece flange on the additional internal protective tube are engaged to one another and secured on the sealing seat; and
wherein the additional internal protective tube includes a shoulder section, wherein a first ceramic disk having a central passage hole for the sensor element is placed in the additional internal protective tube and is supported by the shoulder section of the additional internal protective tube, and wherein a gasket is placed on an end of the first ceramic disk opposite the shoulder section of the additional internal protective tube, the gasket sealingly surrounding the sensor element and pressing against an internal wall of the additional internal protective tube.

11. The sensor as recited in claim 10, wherein an opening of the additional internal protective tube on the side of the single-piece flange is covered by a second ceramic disk having a central passage hole for the sensor element, and wherein a gap between the first and second ceramic disks is filled by the gasket.

\* \* \* \* \*